(12) United States Patent
Kami

(10) Patent No.: US 10,748,655 B2
(45) Date of Patent: Aug. 18, 2020

(54) CENTRAL CONTROL APPARATUS

(71) Applicant: OLYMPUS CORPORATION, Hachioji-shi, Tokyo (JP)

(72) Inventor: Kuniaki Kami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/353,304

(22) Filed: Mar. 14, 2019

(65) Prior Publication Data

US 2019/0206567 A1    Jul. 4, 2019

Related U.S. Application Data

(63) Continuation of application No. PCT/JP2017/009526, filed on Mar. 9, 2017.

(30) Foreign Application Priority Data

Sep. 20, 2016   (JP) .................... 2016-183248

(51) Int. Cl.
*A61B 34/10*        (2016.01)
*G16H 40/67*        (2018.01)
(Continued)

(52) U.S. Cl.
CPC .......... *G16H 40/67* (2018.01); *A61B 1/0005* (2013.01); *A61B 1/00006* (2013.01);
(Continued)

(58) Field of Classification Search
CPC ........ G16H 40/67; A61B 34/10; A61B 90/37; A61B 90/361; A61B 18/14; A61B 1/04; G02B 23/24; G08B 5/36; G06F 11/34
(Continued)

(56) References Cited

U.S. PATENT DOCUMENTS 7,062,343 B2 *  6/2006  Ogushi .............. G03F 7/70525
                                                           700/110
7,333,867 B2 *  2/2008  Kitamoto ........... G05B 19/4184
                                                           700/110
(Continued)

FOREIGN PATENT DOCUMENTS

JP       2003-22116 A      1/2003
JP       2005-275942 A    10/2005
(Continued)

OTHER PUBLICATIONS

May 30, 2017 International Search Report issued in International Patent Application No. PCT/JP2017/009526.

*Primary Examiner* — Hung T Nguyen
(74) *Attorney, Agent, or Firm* — Oliff PLC

(57) ABSTRACT

A system controller configured to centrally control control target devices used in surgery includes a communicating device capable of communicating with a plurality of control target devices, an extraction condition memory capable of storing extraction conditions, and a processor including hardware. The processor detects an abnormal state of connected control target devices. The processor performs recording processing for recording operation information relating to operation on the control target devices as log data into a predetermined storage apparatus. When a device abnormality detecting section detects an abnormal state, the processor extracts relevant information related to the abnormal state from log data.

6 Claims, 16 Drawing Sheets

| DEVICE NAME | EVENT | FIRST EXTRACTION TYPE | FIRST PARAMETER | SECOND EXTRACTION TYPE | SECOND PARAMETER | THIRD EXTRACTION TYPE | THIRD PARAMETER |
|---|---|---|---|---|---|---|---|
| VIDEO SWITCHER | Status Error | B | 5 | C | 1 | A | 3 |
| PNEUMOPERITONEUM DEVICE | Status Error | B | 3 | A | 5 | C | 2 |
| ENDOSCOPE APPARATUS | Status Error | B | 3 | C | 3 | A | 10 |
| . | . | . | . | . | . | . | . |
| . | . | . | . | . | . | . | . |
| . | . | . | . | . | . | . | . |

TBL

(51) Int. Cl.
| | |
|---|---|
| *G08B 5/36* | (2006.01) |
| *A61B 1/00* | (2006.01) |
| *A61B 90/00* | (2016.01) |
| *A61B 18/14* | (2006.01) |
| *G02B 23/24* | (2006.01) |
| *A61B 1/045* | (2006.01) |
| *A61B 17/00* | (2006.01) |

(52) U.S. Cl.
CPC ...... *A61B 1/00016* (2013.01); *A61B 1/00039* (2013.01); *A61B 1/00055* (2013.01); *A61B 1/045* (2013.01); *A61B 18/14* (2013.01); *A61B 34/10* (2016.02); *A61B 90/361* (2016.02); *A61B 90/37* (2016.02); *G02B 23/24* (2013.01); *G08B 5/36* (2013.01); *A61B 2017/00119* (2013.01); *A61B 2017/00221* (2013.01)

(58) Field of Classification Search
USPC .......... 340/635, 539.12, 286.07, 679, 573.3, 340/3.43; 700/96, 121
See application file for complete search history.

(56) References Cited

U.S. PATENT DOCUMENTS

| | | |
|---|---|---|
| 2003/0023340 A1 | 1/2003 | Kitamoto et al. |
| 2006/0206229 A1 | 9/2006 | Kitamoto et al. |
| 2006/0241803 A1 | 10/2006 | Kitamoto et al. |

FOREIGN PATENT DOCUMENTS

| | | |
|---|---|---|
| JP | 2009-116499 A | 5/2009 |
| JP | 2009-189654 A | 8/2009 |

\* cited by examiner

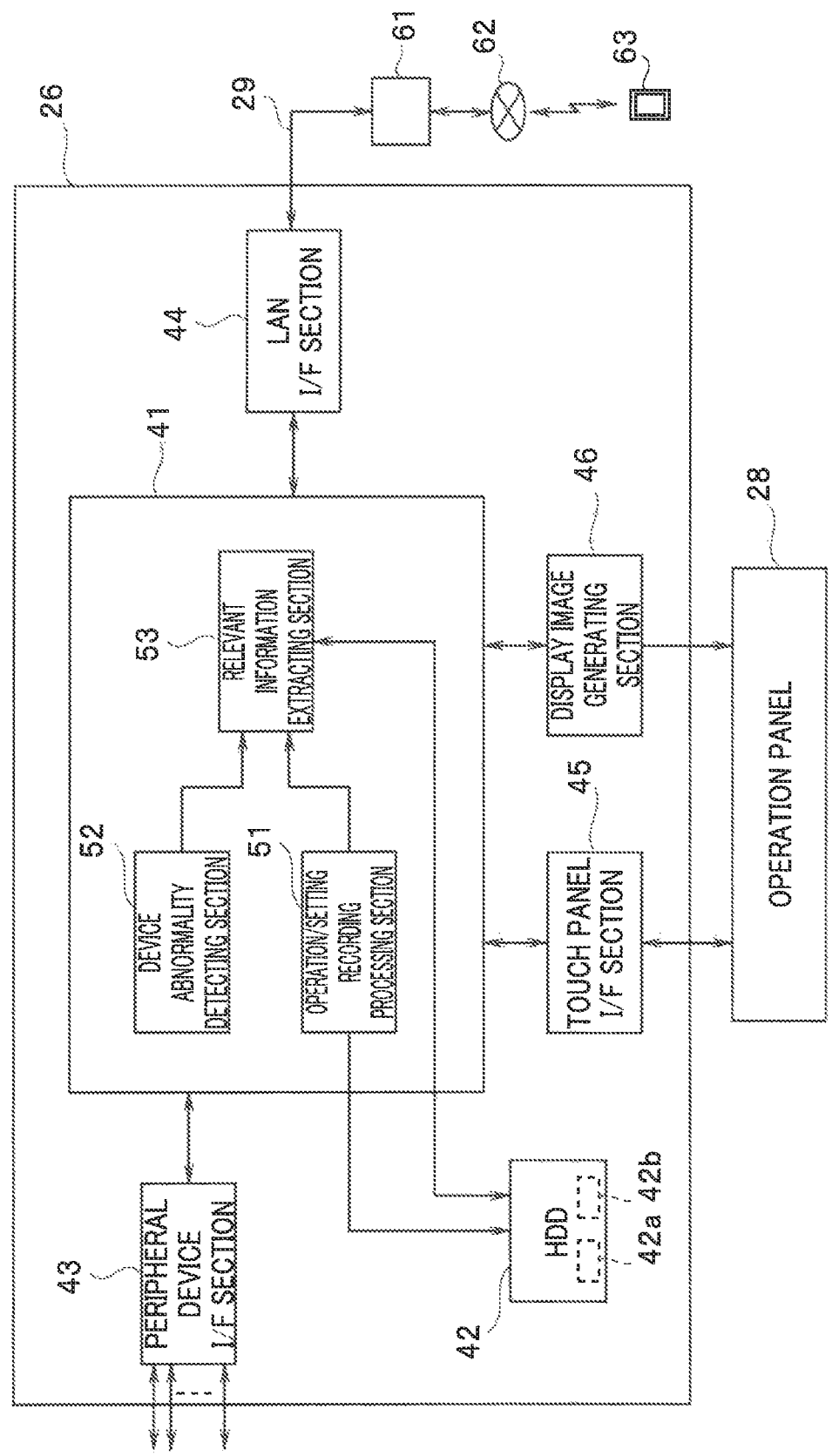

FIG. 4

| DATE | TIME | LOG TYPE | DEVICE ID | DEVICE NAME | Function | Value | OPERATION DIRECTION (From) | GROUP |
|---|---|---|---|---|---|---|---|---|
| 2016/4/23 | 10:18:24 | Logon | 12000 | CONTROLLER | — | — | — | 0 |
| 2016/4/23 | 10:18:26 | Connect | 12001 | PNEUMOPERITONEUM DEVICE | — | — | CONTROLLER | 2 |
| 2016/4/23 | 10:18:38 | Connect | 12002 | ELECTRIC SCALPEL APPARATUS | — | — | CONTROLLER | 2 |
| 2016/4/23 | 10:18:50 | Status Change | 12002 | ELECTRIC SCALPEL APPARATUS | BIPOLAR Cut Output | 5 | CONTROLLER | 2 |
| 2016/4/23 | 10:19:14 | Status Change | 12000 | CONTROLLER | haien mode | 2 | — | 0 |
| 2016/4/23 | 10:19:17 | Status Change | 12003 | ENDOSCOPE APPARATUS | Status Change | W/B OK | DEVICE | 1 |
| 2016/4/23 | 10:19:22 | Status Change | 12003 | ENDOSCOPE APPARATUS | color mode | 2 | CONTROLLER | 1 |
| 2016/4/23 | 10:19:27 | Status Change | 12004 | RECORDER | REC | 1 | CONTROLLER | 1 |
| 2016/4/23 | 10:19:31 | Connect | 12005 | INDOOR CAMERA | Preset | 3 | CONTROLLER | 1 |
| 2016/4/23 | 10:19:37 | Status Change | 12006 | VIDEO SWITCHER | Input Port No. | 1 | CONTROLLER | 1 |
| 2016/4/23 | 10:19:39 | Status Change | 12006 | VIDEO SWITCHER | Output Port No. | 1 | CONTROLLER | 1 |
| 2016/4/23 | 10:19:41 | Status Change | 12006 | VIDEO SWITCHER | Input Port No. | 2 | CONTROLLER | 1 |
| 2016/4/23 | 10:19:42 | Status Change | 12006 | VIDEO SWITCHER | Output Port No. | 2 | CONTROLLER | 1 |
| 2016/4/23 | 10:19:43 | Status Change | 12006 | VIDEO SWITCHER | Input Port No. | 3 | CONTROLLER | 1 |
| 2016/4/23 | 10:19:44 | Status Change | 12006 | VIDEO SWITCHER | Output Port No. | 3 | CONTROLLER | 1 |
| 2016/4/23 | 10:19:56 | Status Change | 12003 | ENDOSCOPE APPARATUS | Enhance | 3 | CONTROLLER | 1 |
| 2016/4/23 | 10:20:06 | Status Change | 12001 | PNEUMOPERITONEUM DEVICE | Insufflation | Start | CONTROLLER | 2 |
| 2016/4/23 | 10:20:11 | Status Change | 12001 | PNEUMOPERITONEUM DEVICE | Pressure | 5 | CONTROLLER | 2 |
| 2016/4/23 | 10:20:48 | Status Change | 12001 | PNEUMOPERITONEUM DEVICE | Pressure | 5 | DEVICE | 2 |
| 2016/4/23 | 10:21:42 | Status Change | 12002 | ELECTRIC SCALPEL APPARATUS | BIPOLAR Cut Output | 5 | CONTROLLER | 2 |
| 2016/4/23 | 10:21:54 | Status Change | 12006 | VIDEO SWITCHER | Input Port No. | 3 | DEVICE | 1 |
| 2016/4/23 | 10:21:55 | Status Change | 12006 | VIDEO SWITCHER | Output Port No. | 6 | DEVICE | 1 |
| 2016/4/23 | 10:22:10 | Status Change | 12002 | ELECTRIC SCALPEL APPARATUS | BIPOLAR Cut Output | 4 | CONTROLLER | 2 |
| 2016/4/23 | 10:22:22 | Status Error | 12006 | VIDEO SWITCHER | Output Port Error | no sync | DEVICE | 1 |

FIG. 7

| DEVICE NAME | EVENT | FIRST EXTRACTION TYPE | FIRST PARAMETER | SECOND EXTRACTION TYPE | SECOND PARAMETER | THIRD EXTRACTION TYPE | THIRD PARAMETER |
|---|---|---|---|---|---|---|---|
| VIDEO SWITCHER | Status Error | B | 5 | C | 1 | A | 3 |
| PNEUMOPERITONEUM DEVICE | Status Error | B | 3 | A | 5 | C | 2 |
| ENDOSCOPE APPARATUS | Status Error | B | 3 | C | 3 | A | 10 |
| ... | ... | ... | ... | ... | ... | ... | ... |

TBL

FIG. 8

| DATE | TIME | LOG TYPE | DEVICE ID | DEVICE NAME | Function | Value | OPERATION DIRECTION (From) | GROUP |
|---|---|---|---|---|---|---|---|---|
| 2016/4/23 | 10:18:24 | Logon | 12000 | CONTROLLER | — | — | — | 0 |
| 2016/4/23 | 10:18:26 | Connect | 12001 | PNEUMOPERITONEUM DEVICE | — | — | CONTROLLER | 2 |
| 2016/4/23 | 10:18:38 | Connect | 12002 | ELECTRIC SCALPEL APPARATUS | — | — | CONTROLLER | 2 |
| 2016/4/23 | 10:18:50 | Status Change | 12002 | ELECTRIC SCALPEL APPARATUS | BIPOLAR Cut Output | 5 | CONTROLLER | 2 |
| 2016/4/23 | 10:19:14 | Status Change | 12000 | CONTROLLER | haien mode | 2 | — | 0 |
| 2016/4/23 | 10:19:17 | Status Change | 12003 | ENDOSCOPE APPARATUS | Status Change | W/B OK | DEVICE | 1 |
| 2016/4/23 | 10:19:22 | Status Change | 12003 | ENDOSCOPE APPARATUS | color mode | 2 | CONTROLLER | 1 |
| 2016/4/23 | 10:19:27 | Status Change | 12004 | RECORDER | REC | 1 | CONTROLLER | 1 |
| 2016/4/23 | 10:19:31 | Connect | 12005 | INDOOR CAMERA | Preset | 3 | CONTROLLER | 1 |
| 2016/4/23 | 10:19:37 | Status Change | 12006 | VIDEO SWITCHER | Input Port No. | 1 | CONTROLLER | 1 |
| 2016/4/23 | 10:19:39 | Status Change | 12006 | VIDEO SWITCHER | Output Port No. | 1 | CONTROLLER | 1 |
| 2016/4/23 | 10:19:41 | Status Change | 12006 | VIDEO SWITCHER | Input Port No. | 2 | CONTROLLER | 1 |
| 2016/4/23 | 10:19:42 | Status Change | 12006 | VIDEO SWITCHER | Output Port No. | 2 | CONTROLLER | 1 |
| 2016/4/23 | 10:19:43 | Status Change | 12006 | VIDEO SWITCHER | Input Port No. | 3 | CONTROLLER | 1 |
| 2016/4/23 | 10:19:44 | Status Change | 12006 | VIDEO SWITCHER | Output Port No. | 3 | CONTROLLER | 1 |
| 2016/4/23 | 10:19:56 | Status Change | 12003 | ENDOSCOPE APPARATUS | Enhance | 3 | CONTROLLER | 1 |
| 2016/4/23 | 10:20:06 | Status Change | 12001 | PNEUMOPERITONEUM DEVICE | Insufflation | Start | CONTROLLER | 2 |
| 2016/4/23 | 10:20:11 | Status Change | 12001 | PNEUMOPERITONEUM DEVICE | Pressure | 5 | CONTROLLER | 2 |
| 2016/4/23 | 10:20:48 | Status Change | 12001 | PNEUMOPERITONEUM DEVICE | Pressure | 5 | DEVICE | 2 |
| 2016/4/23 | 10:21:42 | Status Change | 12002 | ELECTRIC SCALPEL APPARATUS | BIPOLAR Cut Output | 5 | CONTROLLER | 2 |
| 2016/4/23 | 10:21:54 | Status Change | 12006 | VIDEO SWITCHER | Input Port No. | 3 | DEVICE | 1 |
| 2016/4/23 | 10:21:55 | Status Change | 12006 | VIDEO SWITCHER | Output Port No. | 6 | DEVICE | 1 |
| 2016/4/23 | 10:22:10 | Status Change | 12002 | ELECTRIC SCALPEL APPARATUS | BIPOLAR Cut Output | 4 | CONTROLLER | 2 |
| 2016/4/23 | 10:22:22 | Status Error | 12006 | VIDEO SWITCHER | Output Port Error | no sync | DEVICE | 1 |

FIG. 9

| DATE | TIME | LOG TYPE | DEVICE ID | DEVICE NAME | Function | Value | OPERATION DIRECTION (From) | GROUP |
|---|---|---|---|---|---|---|---|---|
| 2016/4/23 | 10:18:24 | Logon | 12000 | CONTROLLER | — | — | — | 0 |
| 2016/4/23 | 10:18:26 | Connect | 12001 | PNEUMOPERITONEUM DEVICE | — | — | CONTROLLER | 2 |
| 2016/4/23 | 10:18:38 | Connect | 12002 | ELECTRIC SCALPEL APPARATUS | — | — | CONTROLLER | 2 |
| 2016/4/23 | 10:18:50 | Status Change | 12002 | ELECTRIC SCALPEL APPARATUS | BIPOLAR Cut Output | 5 | CONTROLLER | 2 |
| 2016/4/23 | 10:19:14 | Status Change | 12000 | CONTROLLER | haien mode | 2 | — | 0 |
| 2016/4/23 | 10:19:17 | Status Change | 12003 | ENDOSCOPE APPARATUS | Status Change | W/B OK | DEVICE | 1 |
| 2016/4/23 | 10:19:22 | Status Change | 12003 | ENDOSCOPE APPARATUS | color mode | 2 | CONTROLLER | 1 |
| 2016/4/23 | 10:19:27 | Status Change | 12004 | RECORDER | REC | 1 | CONTROLLER | 1 |
| 2016/4/23 | 10:19:31 | Connect | 12005 | INDOOR CAMERA | Preset | 3 | CONTROLLER | 1 |
| 2016/4/23 | 10:19:37 | Status Change | 12006 | VIDEO SWITCHER | Input Port No. | 1 | CONTROLLER | 1 |
| 2016/4/23 | 10:19:39 | Status Change | 12006 | VIDEO SWITCHER | Output Port No. | 1 | CONTROLLER | 1 |
| 2016/4/23 | 10:19:41 | Status Change | 12006 | VIDEO SWITCHER | Input Port No. | 2 | CONTROLLER | 1 |
| 2016/4/23 | 10:19:42 | Status Change | 12006 | VIDEO SWITCHER | Output Port No. | 2 | CONTROLLER | 1 |
| 2016/4/23 | 10:19:43 | Status Change | 12006 | VIDEO SWITCHER | Input Port No. | 3 | CONTROLLER | 1 |
| 2016/4/23 | 10:19:44 | Status Change | 12006 | VIDEO SWITCHER | Output Port No. | 3 | CONTROLLER | 1 |
| 2016/4/23 | 10:19:56 | Status Change | 12003 | ENDOSCOPE APPARATUS | Enhance | 3 | CONTROLLER | 1 |
| 2016/4/23 | 10:20:06 | Status Change | 12001 | PNEUMOPERITONEUM DEVICE | Insufflation | Start | CONTROLLER | 2 |
| 2016/4/23 | 10:20:11 | Status Change | 12001 | PNEUMOPERITONEUM DEVICE | Pressure | 5 | CONTROLLER | 2 |
| 2016/4/23 | 10:20:48 | Status Change | 12001 | PNEUMOPERITONEUM DEVICE | Pressure | 5 | DEVICE | 2 |
| 2016/4/23 | 10:21:42 | Status Change | 12002 | ELECTRIC SCALPEL APPARATUS | BIPOLAR Cut Output | 5 | CONTROLLER | 2 |
| 2016/4/23 | 10:21:54 | Status Change | 12006 | VIDEO SWITCHER | Input Port No. | 3 | DEVICE | 1 |
| 2016/4/23 | 10:21:55 | Status Change | 12006 | VIDEO SWITCHER | Output Port No. | 6 | DEVICE | 1 |
| 2016/4/23 | 10:22:10 | Status Change | 12002 | ELECTRIC SCALPEL APPARATUS | BIPOLAR Cut Output | 4 | CONTROLLER | 2 |
| 2016/4/23 | 10:22:22 | Status Error | 12006 | VIDEO SWITCHER | Output Port Error | no sync | DEVICE | 1 |

FIG. 10

| DATE | TIME | LOG TYPE | DEVICE ID | DEVICE NAME | Function | Value | OPERATION DIRECTION (From) | GROUP |
|---|---|---|---|---|---|---|---|---|
| 2016/4/23 | 10:18:24 | Logon | 12000 | CONTROLLER | — | — | — | 0 |
| 2016/4/23 | 10:18:26 | Connect | 12001 | PNEUMOPERITONEUM DEVICE | — | — | CONTROLLER | 2 |
| 2016/4/23 | 10:18:38 | Connect | 12002 | ELECTRIC SCALPEL APPARATUS | — | — | CONTROLLER | 2 |
| 2016/4/23 | 10:18:50 | Status Change | 12002 | ELECTRIC SCALPEL APPARATUS | BiPOLAR Cut Output | 5 | CONTROLLER | 2 |
| 2016/4/23 | 10:19:14 | Status Change | 12000 | CONTROLLER | haien_mode | 2 | — | 0 |
| 2016/4/23 | 10:19:17 | Status Change | 12003 | ENDOSCOPE APPARATUS | Status Change | W/B OK | DEVICE | 1 |
| 2016/4/23 | 10:19:22 | Status Change | 12003 | ENDOSCOPE APPARATUS | color mode | 2 | CONTROLLER | 1 |
| 2016/4/23 | 10:19:27 | Status Change | 12004 | RECORDER | REC | 1 | CONTROLLER | 1 |
| 2016/4/23 | 10:19:31 | Connect | 12005 | INDOOR CAMERA | Preset | 3 | CONTROLLER | 1 |
| 2016/4/23 | 10:19:37 | Status Change | 12006 | VIDEO SWITCHER | Input Port No. | 1 | CONTROLLER | 1 |
| 2016/4/23 | 10:19:39 | Status Change | 12006 | VIDEO SWITCHER | Output Port No. | 2 | CONTROLLER | 1 |
| 2016/4/23 | 10:19:41 | Status Change | 12006 | VIDEO SWITCHER | Input Port No. | 2 | CONTROLLER | 1 |
| 2016/4/23 | 10:19:42 | Status Change | 12006 | VIDEO SWITCHER | Output Port No. | 3 | CONTROLLER | 1 |
| 2016/4/23 | 10:19:43 | Status Change | 12006 | VIDEO SWITCHER | Input Port No. | 3 | CONTROLLER | 1 |
| 2016/4/23 | 10:19:44 | Status Change | 12006 | VIDEO SWITCHER | Output Port No. | 3 | CONTROLLER | 1 |
| 2016/4/23 | 10:19:56 | Status Change | 12003 | ENDOSCOPE APPARATUS | Enhance | 3 | CONTROLLER | 1 |
| 2016/4/23 | 10:20:06 | Status Change | 12001 | PNEUMOPERITONEUM DEVICE | Insufflation | Start | CONTROLLER | 2 |
| 2016/4/23 | 10:20:11 | Status Change | 12001 | PNEUMOPERITONEUM DEVICE | Pressure | 5 | CONTROLLER | 2 |
| 2016/4/23 | 10:20:48 | Status Change | 12001 | PNEUMOPERITONEUM DEVICE | Pressure | 5 | DEVICE | 2 |
| 2016/4/23 | 10:21:42 | Status Change | 12002 | ELECTRIC SCALPEL APPARATUS | BiPOLAR Cut Output | 5 | CONTROLLER | 2 |
| 2016/4/23 | 10:21:54 | Status Change | 12006 | VIDEO SWITCHER | Input Port No. | 3 | DEVICE | 1 |
| 2016/4/23 | 10:21:55 | Status Change | 12006 | VIDEO SWITCHER | Output Port No. | 6 | DEVICE | 1 |
| 2016/4/23 | 10:22:10 | Status Change | 12002 | ELECTRIC SCALPEL APPARATUS | BiPOLAR Cut Output | 4 | CONTROLLER | 2 |
| 2016/4/23 | 10:22:22 | Status Error | 12006 | VIDEO SWITCHER | Output Port Error | no sync | DEVICE | 1 |

FIG. 11

| DATE | TIME | LOG TYPE | DEVICE ID | DEVICE NAME | Function | Value | OPERATION DIRECTION (From) | GROUP |
|---|---|---|---|---|---|---|---|---|
| 2016/6/21 | 13:10:00 | Status Change | 12006 | VIDEO SWITCHER | Input Port No. | 1 | CONTROLLER | 1 |
| 2016/6/21 | 13:10:01 | Status Change | 12006 | VIDEO SWITCHER | Output Port No. | 1 | CONTROLLER | 1 |
| 2016/6/21 | 13:10:02 | Status Change | 12006 | VIDEO SWITCHER | Input Port No. | 2 | CONTROLLER | 1 |
| 2016/6/21 | 13:10:03 | Status Change | 12006 | VIDEO SWITCHER | Output Port No. | 2 | CONTROLLER | 1 |
| 2016/6/21 | 13:10:04 | Status Change | 12006 | VIDEO SWITCHER | Input Port No. | 3 | CONTROLLER | 1 |
| 2016/6/21 | 13:10:05 | Status Change | 12006 | VIDEO SWITCHER | Output Port No. | 3 | CONTROLLER | 1 |
| 2016/6/21 | 13:10:15 | Connect | 12005 | INDOOR CAMERA | Preset | 3 | CONTROLLER | 2 |
| 2016/6/21 | 13:10:25 | Status Change | 12003 | ENDOSCOPE APPARATUS | color mode | 1 | CONTROLLER | 3 |
| 2016/6/21 | 13:10:35 | Status Change | 12007 | LIGHT SOURCE APPARATUS | Status Change | color mode 1 | DEVICE | 3 |
| 2016/6/21 | 13:11:00 | Status Change | 12003 | ENDOSCOPE APPARATUS | Status Change | W/B OK | DEVICE | 3 |
| 2016/6/21 | 13:11:01 | Status Change | 12001 | PNEUMOPERITONEUM DEVICE | Insufflation | Start | CONTROLLER | 4 |
| 2016/6/21 | 13:11:04 | Status Change | 12004 | RECORDER | REC | 1 | CONTROLLER | 2 |
| 2016/6/21 | 13:11:05 | Status Change | 12001 | PNEUMOPERITONEUM DEVICE | Pressure | 5 | CONTROLLER | 4 |
| 2016/6/21 | 13:11:06 | Status Change | 12001 | PNEUMOPERITONEUM DEVICE | Pressure | 5 | DEVICE | 4 |
| 2016/6/21 | 13:11:07 | Status Change | 12003 | ENDOSCOPE APPARATUS | color mode | 2 | CONTROLLER | 3 |
| 2016/6/21 | 13:11:08 | Status Change | 12007 | LIGHT SOURCE APPARATUS | Status Change | color mode 2 | DEVICE | 3 |
| 2016/6/21 | 13:17:08 | Status Change | 12002 | ELECTRIC SCALPEL APPARATUS | BIPOLAR Cut | 5 | CONTROLLER | 4 |
| 2016/6/21 | 13:20:08 | Status Change | 12002 | ELECTRIC SCALPEL APPARATUS | Status Change | BIPOLAR Cut 5 | DEVICE | 4 |
| 2016/6/21 | 13:20:18 | Status Change | 12007 | LIGHT SOURCE APPARATUS | Status Change | color mode 1 | DEVICE | 3 |
| 2016/6/21 | 13:20:25 | Status Error | 12003 | ENDOSCOPE APPARATUS | Status Error | color mode mismatch | DEVICE | 3 |

FIG. 12

| DATE | TIME | LOG TYPE | DEVICE ID | DEVICE NAME | Function | Value | OPERATION DIRECTION (From) | GROUP |
|---|---|---|---|---|---|---|---|---|
| 2016/6/21 | 13:10:00 | Status Change | 12006 | VIDEO SWITCHER | Input Port No. | 1 | CONTROLLER | 1 |
| 2016/6/21 | 13:10:01 | Status Change | 12006 | VIDEO SWITCHER | Output Port No. | 1 | CONTROLLER | 1 |
| 2016/6/21 | 13:10:02 | Status Change | 12006 | VIDEO SWITCHER | Input Port No. | 2 | CONTROLLER | 1 |
| 2016/6/21 | 13:10:03 | Status Change | 12006 | VIDEO SWITCHER | Output Port No. | 2 | CONTROLLER | 1 |
| 2016/6/21 | 13:10:04 | Status Change | 12006 | VIDEO SWITCHER | Input Port No. | 3 | CONTROLLER | 1 |
| 2016/6/21 | 13:10:05 | Status Change | 12006 | VIDEO SWITCHER | Output Port No. | 3 | CONTROLLER | 1 |
| 2016/6/21 | 13:10:15 | Connect | 12005 | INDOOR CAMERA | Preset | 3 | CONTROLLER | 2 |
| 2016/6/21 | 13:10:25 | Status Change | 12003 | ENDOSCOPE APPARATUS | color mode | 1 | CONTROLLER | 3 |
| 2016/6/21 | 13:10:35 | Status Change | 12007 | LIGHT SOURCE APPARATUS | Status Change | color mode 1 | DEVICE | 3 |
| 2016/6/21 | 13:11:00 | Status Change | 12003 | ENDOSCOPE APPARATUS | Status Change | W/B OK | DEVICE | 3 |
| 2016/6/21 | 13:11:01 | Status Change | 12001 | PNEUMOPERITONEUM DEVICE | Insufflation | Start | CONTROLLER | 4 |
| 2016/6/21 | 13:11:04 | Status Change | 12004 | RECORDER | REC | 1 | CONTROLLER | 2 |
| 2016/6/21 | 13:11:05 | Status Change | 12001 | PNEUMOPERITONEUM DEVICE | Pressure | 5 | CONTROLLER | 4 |
| 2016/6/21 | 13:11:06 | Status Change | 12001 | PNEUMOPERITONEUM DEVICE | Pressure | 5 | DEVICE | 4 |
| 2016/6/21 | 13:11:07 | Status Change | 12003 | ENDOSCOPE APPARATUS | color mode | 2 | CONTROLLER | 3 |
| 2016/6/21 | 13:11:08 | Status Change | 12007 | LIGHT SOURCE APPARATUS | Status Change | color mode 2 | DEVICE | 3 |
| 2016/6/21 | 13:17:08 | Status Change | 12002 | ELECTRIC SCALPEL APPARATUS | BIPOLAR Cut | BIPOLAR Cut 5 | CONTROLLER | 4 |
| 2016/6/21 | 13:20:08 | Status Change | 12002 | ELECTRIC SCALPEL APPARATUS | Status Change | 5 | DEVICE | 4 |
| 2016/6/21 | 13:20:18 | Status Change | 12007 | LIGHT SOURCE APPARATUS | Status Change | color mode 1 | DEVICE | 3 |
| 2016/6/21 | 13:20:25 | Status Error | 12003 | ENDOSCOPE APPARATUS | Status Error | color mode mismatch | DEVICE | 3 |

FIG. 13

| DATE | TIME | LOG TYPE | DEVICE ID | DEVICE NAME | Function | Value | OPERATION DIRECTION (From) | GROUP |
|---|---|---|---|---|---|---|---|---|
| 2016/6/21 | 13:10:00 | Status Change | 12006 | VIDEO SWITCHER | Input Port No. | 1 | CONTROLLER | 1 |
| 2016/6/21 | 13:10:01 | Status Change | 12006 | VIDEO SWITCHER | Output Port No. | 1 | CONTROLLER | 1 |
| 2016/6/21 | 13:10:02 | Status Change | 12006 | VIDEO SWITCHER | Input Port No. | 2 | CONTROLLER | 1 |
| 2016/6/21 | 13:10:03 | Status Change | 12006 | VIDEO SWITCHER | Output Port No. | 2 | CONTROLLER | 1 |
| 2016/6/21 | 13:10:04 | Status Change | 12006 | VIDEO SWITCHER | Input Port No. | 3 | CONTROLLER | 1 |
| 2016/6/21 | 13:10:05 | Status Change | 12006 | VIDEO SWITCHER | Output Port No. | 3 | CONTROLLER | 1 |
| 2016/6/21 | 13:10:15 | Connect | 12005 | INDOOR CAMERA | Preset | 3 | CONTROLLER | 2 |
| 2016/6/21 | 13:10:25 | Status Change | 12003 | ENDOSCOPE APPARATUS | color mode | 1 | CONTROLLER | 3 |
| 2016/6/21 | 13:10:35 | Status Change | 12007 | LIGHT SOURCE APPARATUS | Status Change | color mode 1 | DEVICE | 3 |
| 2016/6/21 | 13:11:00 | Status Change | 12003 | ENDOSCOPE APPARATUS | Status Change | W/B OK | DEVICE | 3 |
| 2016/6/21 | 13:11:01 | Status Change | 12001 | PNEUMOPERITONEUM DEVICE | Insufflation | Start | CONTROLLER | 4 |
| 2016/6/21 | 13:11:04 | Status Change | 12004 | RECORDER | REC | 1 | CONTROLLER | 2 |
| 2016/6/21 | 13:11:05 | Status Change | 12001 | PNEUMOPERITONEUM DEVICE | Pressure | 5 | CONTROLLER | 4 |
| 2016/6/21 | 13:11:06 | Status Change | 12001 | PNEUMOPERITONEUM DEVICE | Pressure | 5 | DEVICE | 4 |
| 2016/6/21 | 13:11:07 | Status Change | 12003 | ENDOSCOPE APPARATUS | color mode | 2 | CONTROLLER | 3 |
| 2016/6/21 | 13:11:08 | Status Change | 12007 | LIGHT SOURCE APPARATUS | Status Change | color mode 2 | DEVICE | 3 |
| 2016/6/21 | 13:17:08 | Status Change | 12002 | ELECTRIC SCALPEL APPARATUS | BIPOLAR Cut | 5 | CONTROLLER | 4 |
| 2016/6/21 | 13:20:08 | Status Change | 12002 | ELECTRIC SCALPEL APPARATUS | Status Change | BIPOLAR Cut 5 | DEVICE | 4 |
| 2016/6/21 | 13:20:18 | Status Change | 12007 | LIGHT SOURCE APPARATUS | Status Change | color mode 1 | DEVICE | 3 |
| 2016/6/21 | 13:20:25 | Status Error | 12003 | ENDOSCOPE APPARATUS | Status Error | color mode mismatch | DEVICE | 3 |

FIG. 14

| DATE | TIME | LOG TYPE | DEVICE ID | DEVICE NAME | Function | Value | OPERATION DIRECTION (From) | GROUP |
|---|---|---|---|---|---|---|---|---|
| 2016/6/21 | 13:10:00 | Status Change | 12006 | VIDEO SWITCHER | Input Port No. | 1 | CONTROLLER | 1 |
| 2016/6/21 | 13:10:01 | Status Change | 12006 | VIDEO SWITCHER | Output Port No. | 1 | CONTROLLER | 1 |
| 2016/6/21 | 13:10:02 | Status Change | 12006 | VIDEO SWITCHER | Input Port No. | 2 | CONTROLLER | 1 |
| 2016/6/21 | 13:10:03 | Status Change | 12006 | VIDEO SWITCHER | Output Port No. | 2 | CONTROLLER | 1 |
| 2016/6/21 | 13:10:04 | Status Change | 12006 | VIDEO SWITCHER | Input Port No. | 3 | CONTROLLER | 1 |
| 2016/6/21 | 13:10:05 | Status Change | 12006 | VIDEO SWITCHER | Output Port No. | 3 | CONTROLLER | 1 |
| 2016/6/21 | 13:10:15 | Connect | 12005 | INDOOR CAMERA | Preset | 3 | CONTROLLER | 2 |
| 2016/6/21 | 13:10:25 | Status Change | 12003 | ENDOSCOPE APPARATUS | color mode | 1 | CONTROLLER | 3 |
| 2016/6/21 | 13:10:35 | Status Change | 12007 | LIGHT SOURCE APPARATUS | Status Change | color mode 1 | DEVICE | 3 |
| 2016/6/21 | 13:11:00 | Status Change | 12003 | ENDOSCOPE APPARATUS | Status Change | W/B OK | DEVICE | 3 |
| 2016/6/21 | 13:11:01 | Status Change | 12001 | PNEUMOPERITONEUM DEVICE | Insufflation | Start | CONTROLLER | 4 |
| 2016/6/21 | 13:11:04 | Status Change | 12004 | RECORDER | REC | 1 | CONTROLLER | 2 |
| 2016/6/21 | 13:11:05 | Status Change | 12001 | PNEUMOPERITONEUM DEVICE | Pressure | 5 | CONTROLLER | 4 |
| 2016/6/21 | 13:11:06 | Status Change | 12001 | PNEUMOPERITONEUM DEVICE | Pressure | 5 | DEVICE | 4 |
| 2016/6/21 | 13:11:07 | Status Change | 12003 | ENDOSCOPE APPARATUS | color mode | 2 | CONTROLLER | 3 |
| 2016/6/21 | 13:11:08 | Status Change | 12007 | LIGHT SOURCE APPARATUS | Status Change | color mode 2 | DEVICE | 3 |
| 2016/6/21 | 13:17:08 | Status Change | 12002 | ELECTRIC SCALPEL APPARATUS | BIPOLAR Cut | 5 | CONTROLLER | 4 |
| 2016/6/21 | 13:20:08 | Status Change | 12002 | ELECTRIC SCALPEL APPARATUS | Status Change | BIPOLAR Cut 5 | DEVICE | 4 |
| 2016/6/21 | 13:20:18 | Status Change | 12007 | LIGHT SOURCE APPARATUS | Status Change | color mode 1 | DEVICE | 3 |
| 2016/6/21 | 13:20:25 | Status Error | 12003 | ENDOSCOPE APPARATUS | Status Error | color mode mismatch | DEVICE | 3 |

TBL1

| OPERATION BUTTON NAME | EXTRACTION TYPE |
|---|---|
| VIDEO SWITCHER | B |
| PNEUMOPERITONEUM DEVICE | B |
| ENDOSCOPE APPARATUS | B |
| ⋮ | ⋮ |
| UNKNOWN | A |

CENTRAL CONTROL APPARATUS

This application is a continuation application of PCT/JP2017/009526 filed on Mar. 9, 2017 and claims benefit of Japanese Application No. 2016-183248 filed in Japan on Sep. 20, 2016, the entire contents of which are incorporated herein by this reference.

BACKGROUND OF THE INVENTION

Field of the Invention

The present invention relates to a central control apparatus, and particularly relates to a central control apparatus that is configured to centrally control control target devices used in surgery.

Description of Related Art

Various kinds of medical devices are used in surgery. The medical devices include an endoscope apparatus, a pneumoperitoneum device, an electric scalpel apparatus, etc., and are centrally controlled by a central control apparatus. Device other than the medical devices, for example, a recorder for recording, etc. may be used in surgery. Therefore, in this case, the central control apparatus performs centralized control including such non-medical devices.

During surgery, an operator, a nurse or the like directly operates an operation button or the like of each medical device, or operates an operation panel or the like connected to the central control apparatus, which makes it possible to give an operation instruction to each medical device.

Incidentally, when an abnormality occurs in the medical device during surgery, an error is displayed on a monitor or the like, and the operator or the like can recognize the abnormality of the device and can take a countermeasure to the abnormality, and if necessary, may contact a person in charge of maintenance or the like to request for pursuit of causes.

Furthermore, a user such as a nurse may sometimes perform an unintended setting operation, and Japanese Patent Application Laid-Open Publication No. 2009-189654 has proposed a system that enables a user to take appropriate measures even when such an unintended setting operation is performed.

In the proposed system, a user's surgical system creates operation setting log data, and transmits the created operation setting log data to a remote system upon receiving a transmission request from an outside. As a result, the external, that is, the remote system can receive and analyze the operation setting log data in the user system.

SUMMARY OF THE INVENTION

A central control apparatus according to an aspect of the present invention includes a communicating device capable of communicating with a plurality of control target devices used in surgery, an extraction condition memory capable of storing extraction conditions related to abnormal states corresponding to types of the plurality of control target devices, and a processor including hardware, wherein the processor detects the abnormal states of the control target devices based on a communication result of the communicating device, performs recording processing for recording operation information relating to operation on the control target devices as log data into a predetermined storage apparatus, and upon detection of an abnormal state of any of the plurality of control target devices, extracts predetermined log data out of the recorded log data as relevant information according to an extraction condition stored in the extraction condition memory and corresponding to a type of a control target device for which the abnormal state is detected, the extraction conditions stored in the extraction condition Memory include a plurality of extraction types that are different in priority order according to the types of the plurality of control target devices, and a plurality of parameter values, and the plurality of extraction types include a type for setting, as the relevant information, log data relating to the control target device for which the abnormal state is detected, and a type for setting, as the relevant information, log data relating to a plurality of control target devices belonging to a group containing the control target device for which the abnormal state is detected.

BRIEF DESCRIPTION OF THE DRAWINGS

FIG. 3 is a block diagram showing a configuration of a system controller according to the embodiment of the present invention;

FIG. 4 is a diagram showing an example of log data recorded in a log table of a hard disk drive of a system controller according to the embodiment of the present invention;

FIG. 7 is a diagram showing an example of an extraction condition table for specifying extraction conditions according to the embodiment of the present invention;

FIG. 8 is a diagram showing log data extracted when an extraction type is "B" according to the embodiment of the present invention;

FIG. 9 is a diagram showing log data extracted when the extraction type is "C" according to the embodiment of the present invention;

FIG. 10 is a diagram showing log data extracted when the extraction type is "A" according to the embodiment of the present invention;

FIG. 11 is a diagram showing another example of log data recorded in a hard disk drive of the system controller according to the embodiment of the present invention;

FIG. 12 is a diagram showing log data extracted when the extraction type is "B" according to the embodiment of the present invention;

FIG. 13 is a diagram showing log data extracted when the extraction type is "C" according to the embodiment of the present invention;

FIG. 14 is a diagram showing log data extracted when the extraction type is "A" according to the embodiment of the present invention;

DETAILED DESCRIPTION OF PREFERRED EMBODIMENTS

An embodiment of the present invention will be described hereinafter with reference to the drawings.

Configuration

Figure 1:
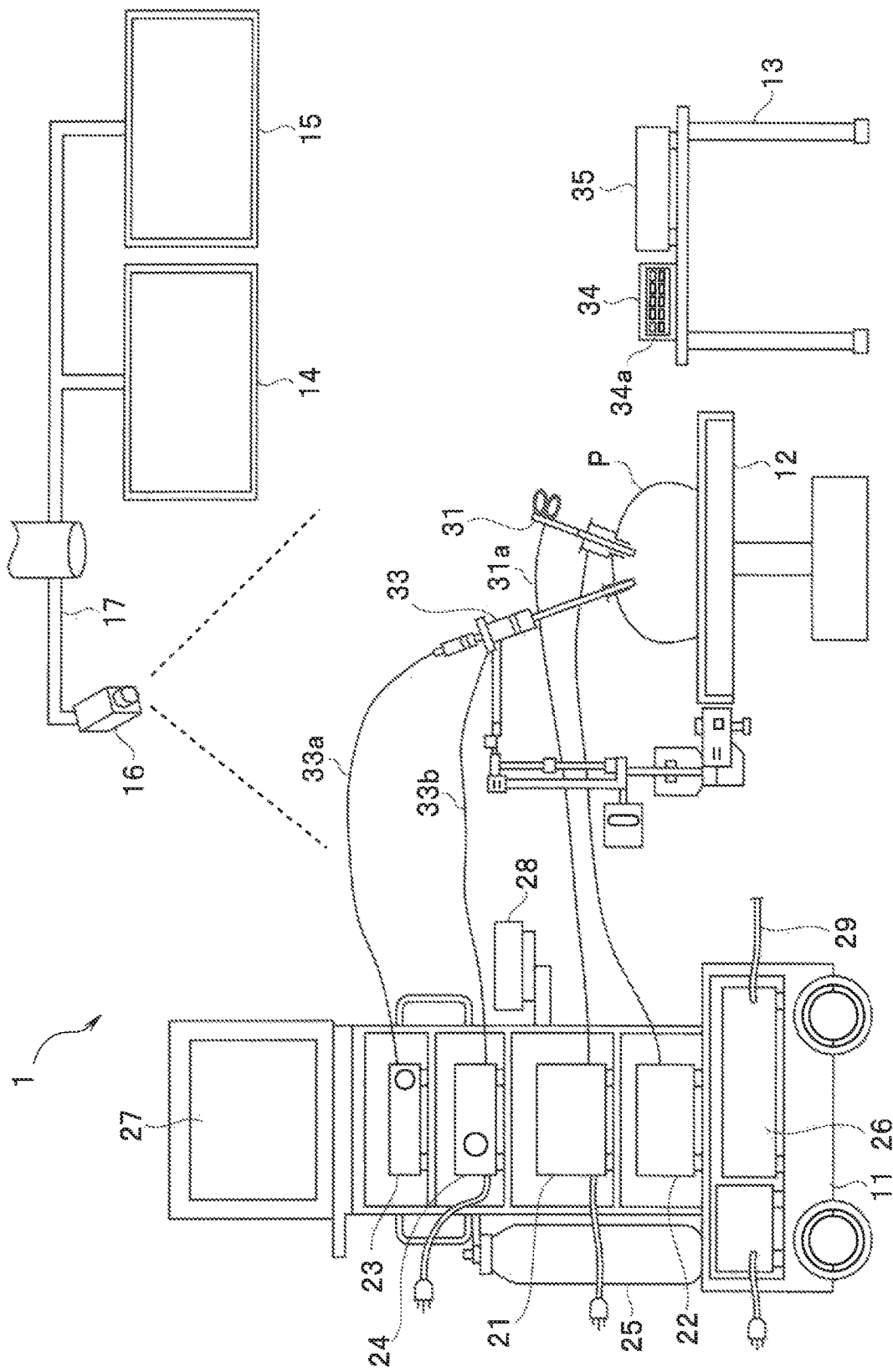
FIG. 1 is a configuration diagram of a surgical system according to an embodiment of the present invention.

FIG. 1 is a configuration diagram of a surgical system according to an embodiment of the present invention. A surgical system 1 includes a plurality of medical devices and a plurality of non-medical devices.

FIG. 1 shows various kinds of devices installed in an operation room, and the surgical system 1 is configured to include various kinds of devices.

As shown in FIG. 1, a cart 11 in which various kinds of devices are mounted, a patient bed 12 on which a patient P lies, a table 13, two monitors 14 and 15 suspended from a ceiling, an indoor camera 16 for photographing the inside of the operation room, and plural shadowless lights and the like (not shown) are arranged at predetermined positions in the operation room. The monitors 14 and 15 as display apparatuses and the indoor camera 16 are fitted to an arm member 17 fixed to the ceiling.

An electric scalpel apparatus 21, a pneumoperitoneum device 22, a video processor for an endoscope (hereinafter referred to as a video processor) 23, a light source apparatus for an endoscope (hereinafter referred to as a light source apparatus) 24 and a gas cylinder 25 filled with carbon dioxide are mounted in the cart 11 as plural kinds of medical devices which are control target apparatuses. Furthermore, various kinds of medical devices such as the electric scalpel apparatus 21 and a system controller 26 are also mounted in the cart 11. The system controller 26 is a central control apparatus configured for centrally controlling various kinds of medical devices and non-medical devices described later.

Furthermore, a monitor 27 is mounted on a top of the cart 11, and an operation panel 28 is fixedly provided on a side surface of the cart 11. The monitor 27 is, for example, a TV monitor configured to display an endoscopic image or the like.

The operation panel 28 is connected to the system controller 26 and configured by, for example, a displaying section such as a liquid crystal display and a touch sensor integrally provided on the displaying section, and also is a central operation apparatus to be operated by a user such as a nurse who is in a non-sterilized room.

A screen for various kinds of operations such as operation such as on/off operation of each device, setting such as parameter input, and change of values of set input parameters is displayed on the operation panel 28.

An electric scalpel 31 is connected to the electric scalpel apparatus 21 via a cable 31a. The electric scalpel 31 is, for example, a bipolar type electric scalpel.

An endoscope 33 is connected to the video processor 23 via a cable 33a, and connected to the light source apparatus 24 via a light guide cable 33b. An endoscope apparatus is configured by the endoscope 33, the video processor 23, and the light source apparatus 24.

The endoscope 33 includes an image pickup device configured to receive reflected light from an object via an observation window provided at a distal end portion of an insertion portion and performs photoelectric conversion on the reflected light. The image pickup device is an image pickup device with a high number of pixels, and outputs an image pickup signal corresponding to 4K video.

Therefore, the video processor 23 also processes the image pickup signal of the 4K video to generate and output a video signal of the 4K video.

The light source apparatus 24 is connected to the video processor 23, and performs a light-adjusting operation according to a light-adjusting signal from the video processor 23. Furthermore, the light source apparatus 24 performs selection control of an internal filler according to an observation mode. For example, in a case where the endoscope 33 is adaptable to two observation modes of a normal light observation mode and a special light observation mode such as an infrared light observation mode, when a user operates the video processor 23 to select an observation mode, a selection signal is outputted to the light source apparatus 24. According to the selection signal, the light source apparatus 24 operates so as to arrange a filter corresponding to the selected observation mode such as an internal color filter on an optical path of illumination light.

A video switcher 34 and a recorder 35 are placed on the table 13.

The video switcher 34 is a device configured to switch output destinations of video signals from the video processor 23, the indoor camera 16 and the recorder 35, and specify which one of the monitors 14, 15 and 27 each image should be displayed on.

The video switcher 34 has an operation portion 34a provided with plural operation buttons configured to switch the output destinations of the respective video signals, and by operating a desired operation button of the operation portion 34a, a user such as a nurse can specify which one of the monitors each image of the video processor 23, the indoor camera 16 and the recorder 35 as video signal sources should be displayed on.

Note that a display switching operation of the video switcher 34 can be also performed on the operation panel 28.

The recorder 35 is an apparatus configured to record an endoscopic image from the video processor 23 and an indoor image of the indoor camera 16.

The system controller 26 is connected to the various devices of the indoor camera 16, the electric scalpel apparatus 21, the pneumoperitoneum device 22, the video processor 23, the light source apparatus 24, the operation panel 28, the video switcher 34, and the recorder 35 via signal lines (not shown).

The operation panel 28 is connected to the system controller 26, and the user can perform an input of operations such as turning-on/off operations of various kinds of devices and change of setting values by touching a desired Operation switch displayed on the operation panel 28.

Furthermore, the user can also perform an input of operations such as turning-on/off operations of various kinds of devices and change of setting values by directly operating the operation buttons of the respective devices such as the video processor 23, the pneumoperitoneum device 22 and the video switcher 34.

Furthermore, the system controller 26 is connected to, for example, a LAN in a hospital via a cable 29. The LAN is also connected to the external Internet. Therefore, the system controller 26 can also send e-mails and the like via the Internet.

As described above, the system controller 26 centrally controls the indoor camera 16, the monitors 14 and 15, the electric scalpel apparatus 21, the pneumoperitoneum device 22, the video processor 23, the light source apparatus 24, the recorder 35, and the shadowless lamps (not shown). Therefore, when communication is being performed between the system controller 26 and each device, the system controller 26 is enabled to display setting states of the connected devices, set screens of the operation switches, etc.

Figure 2:
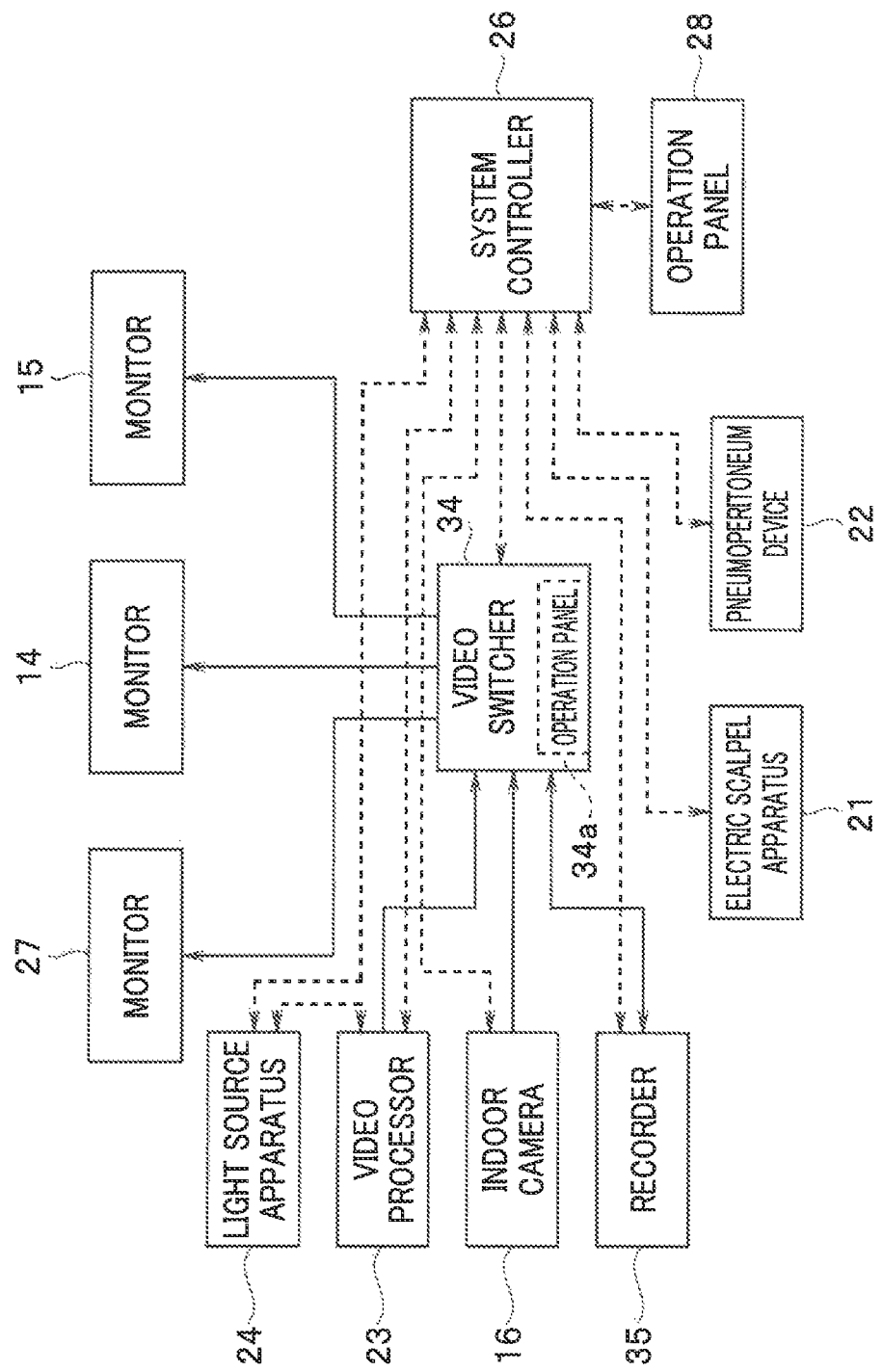
FIG. 2 is a block diagram showing a flow of control signals and video signals among apparatuses of the surgical system according to the embodiment of the present invention.

FIG. 2 is a block diagram showing flows of control signals and video signals among the apparatuses of the surgical system 1. In FIG. 2, the video signals are represented by arrows of solid lines and the control signals are represented by arrows of dotted lines.

The monitors 14, 15, and 27 are connected to the video switcher 34, and three video signals of the indoor camera 16, the video processor 23, and the recorder 35 are supplied to any of the monitors 14, 15, and 27 via the video switcher 34.

As described above, the system controller 26 is connected to the indoor camera 16, the electric scalpel apparatus 21, etc. via signal lines, and is capable of mutually communicating with and controlling the respective devices. That is, the system controller 26 is a central control apparatus configured to centrally control control target devices used in surgery.

Furthermore, as described above, the video processor 23 and the light source apparatus 24 are connected to each other via a signal line, and can mutually communicate with each other to enable a light adjusting operation and the like.

FIG. 3 is a block diagram showing a configuration of the system controller.

The system controller 26 is a computer apparatus including a central processing unit (hereinafter referred to as CPU), and storage apparatuses such as ROM and RAM. Each function of the system controller 26 is achieved by reading out and executing various kinds of programs stored in a memory.

The system controller 26 includes a control section 41, a hard disk drive (HDD) 42, a peripheral device interface (hereinafter abbreviated as I/F) section 43, a LAN I/F section 44, a touch panel I/F section 45, and a display image generating section 46.

The control section 41 is a processor including an operation/setting recording processing section 51, a device abnormality detecting section 52, and a relevant information extracting section 53. Each processing of the operations setting recording processing section 51, the device abnormality detecting section 52, and the relevant information extracting section 53 is achieved by CPU and respective processing programs. The CPU reads from a storage apparatus and executes programs for processing of the operation/ setting recording processing section 51, the device abnormality detecting section 52 and the relevant information extracting section 53 stored in the storage apparatus to achieve the functions of the operation/setting recording processing section 51, the device abnormality detecting section 52, and the relevant information extracting section 53.

Note that in this case, the control section 41 as a processor containing hardware executes the functions of the operation/ setting recording processing section 51, the device abnormality detecting section 52, and the relevant information extracting section 53 by software, but the respective sections for these functions may be configured by individual electronic circuits or may be configured as circuit blocks in an integrated circuit such as FPGA (Field Programmable Gate Array) or the like.

The hard disk drive 42 is a large-capacity memory, and is connected to the control section 41. Image data of the endoscopic image and log data described later are recorded in the hard disk drive 42. Various kinds of processing programs and various kinds of parameter data, etc. for the processing programs may be also recorded in the hard disk drive 42.

The log data described later and extraction condition data described later are stored in the hard disk drive 42.

The peripheral device I/F section 43 is an I/F configured to give and receive data between the control section 41 and a plurality of peripheral devices including the electric scalpel apparatus 21, the pneumoperitoneum device 22, the video processor 23, the light source apparatus 24, the indoor camera 16, the video switcher 34, and the recorder 35. Image data of the endoscopic image, the log data described later, and an error notification are received by the control section 41 via the peripheral device I/F section 43.

The LAN I/F section 44 is an I/F which is connected to the cable 29 connected to the LAN in the hospital, and with which the control section 41 communicates via the LAN.

The system controller 26 can communicate with a server 61 in the hospital via the LAN, and can also connect to the Internet 62 via the server 61. Therefore, the system controller 26 can also send e-mails to a portable tem final apparatus 63 such as a smartphone and a tablet via the Internet 62.

In the present embodiment, the log data and the extraction condition data are stored in the hard disk drive 42, but may be stored in the server 61. By storing the log data and the extraction condition data in the server 61, it is possible to pursue cause of an error notification even in a state where a power supply of the system controller 26 is turned off after the surgery.

The touch panel I/F section 45 is an OF circuit configured to give and receive a signal to the touch sensor on the operation panel 28 and a signal from the touch sensor.

The display image generating section 46 is a circuit configured to generate an image to be displayed on the displaying section such as a liquid crystal display or the like of the operation panel 28, and outputting a generated image signal to the operation panel 28.

The operation/setting recording processing section 51 of the control section 41 is a processing section configured to select operation information on various kinds of operations containing the setting operation from various kinds of signals from the respective devices via the peripheral device I/F section 43, and record the operation information as log data into a log table 42a which is a predetermined storage area of the hard disk drive 42. The hard disk drive 42 further has a storage area 42b in which extraction condition data described later are stored.

That is, the operation/setting recording processing section 51 configures a recording processing section for performing recording processing for recording, as log data into the hard disk drive 42 as a predetermined storage apparatus, operation information on operations to be performed on control target devices which are medical devices and non-medical devices.

The device abnormality detecting section 52 is a processing section configured to receive various kinds of signals from the respective devices via the peripheral devices section 43, select an error notification for notifying an abnormal state of a device from the received signals, and detect abnormality of the device.

That is, the device abnormality detecting section 52 configures an abnormality detecting section configured to detect an abnormal state of the control target devices connected to the system controller 26 which is the central control apparatus.

Furthermore, upon receiving an error notification, the operation/setting recording processing section 51 also records the error notification as log data into the log table 42a.

Therefore, when a user such as a nurse performs a setting operation such as setting of operation or setting of parameter values and each operation such as an on/off operation or an output instruction operation on each device by operating the operation panel 28 or operating an operation button of each device, recording of the operation is recorded as log data into the log table 42a.

Furthermore, when an error occurs in each device, each device transmits an error notification to the system controller 26. Upon receiving the error notification from the device in which the error occurs, the system controller 26 also records the error notification as log data into the log table 42a.

Based on the received error notification, the relevant information extracting section 53 extracts log data corresponding to a predetermined extraction condition from the log data. Specifically, the relevant information extracting section 53 reads out the extraction condition data corresponding to the received error notification from the storage area 42b, and searches the log table 42a according to the read-out extraction condition data to extract relevant information on the error notification.

That is, when the device abnormality detecting section 52 detects an abnormal state, the relevant information extracting section 53 extracts relevant information relating to the detected abnormal state from the log data.

As described later, when receiving an extraction instruction for a device specified by user's predetermined operation on the operation panel 28, the relevant information extracting section 53 reads out extraction condition data corresponding to the extraction instruction from the storage area 42b, and searches the log table 42a based on the read-out extraction condition data to extract relevant information on the extraction instruction.

That is, when receiving the extraction instruction for the log data on the specified control target device, the relevant information extracting section 53 extracts relevant information related to the specified control target device from the log data.

Therefore, the relevant information extracting section 53 configures a relevant information extracting section configured to extract relevant information relating to error information or specified information from the log data.

Action

Next, operation of the system controller 26 will be described.

First, an example of the log data will be described.

FIG. 4 is a diagram showing an example of log data recorded in the log table of the hard disk drive of the system controller.

The log data are stored in the log table 42a in a predetermined storage area of the hard disk drive 42.

The log data are configured in a table format as shown in FIG. 4. Each log data includes respective item data of date, time, log type, device ID (identifier), device name, function, value, operation direction, and group.

As shown in FIG. 4, the log data are stored in the order of occurrence time in the log table 42a.

As described above, the storage area 42b configured to store extraction condition data is also provided in the hard disk drive 42. The extraction condition data can be set from the operation panel 28. The extraction condition is prescribed for each error notification, and preset in the storage area 42b and stored as extraction condition data by an operator or a nurse. The extraction condition will be described later.

Transmission of Log Data When Error Occurs

Figure 5:
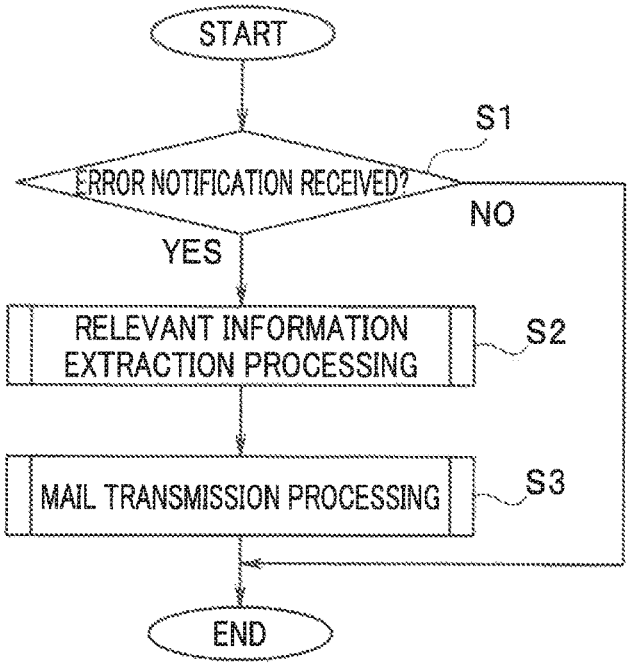
FIG. 5 is a flowchart showing an example of a processing flow of the system controller under occurrence of an error according to the embodiment of the present invention.

FIG. 5 is a flowchart showing an example of a processing flow of the system controller when an error occurs.

The system controller 26 determines whether an error notification is received by the device abnormality detecting section 52 (S1).

For example, when a nurse erroneously operates the operation portion 34a of the video switcher 34 to cause no video signal to be outputted to the monitor 15, the video switcher 34 detects that no video signal is outputted to the monitor 15, that is, detects no signal (no synchronization signal). The video switcher 34 outputs, to the system controller 26, an error signal indicating that a signal output to the monitor 15 is no signal. The system controller 26 receives the error signal in S1.

When no error notification is received (S1: NO), no processing is performed.

When an error notification is received (S1: YES), the system controller 26 performs relevant information extraction processing of extracting relevant information related to the error notification from the log data by the relevant information extracting section 53 (S2).

Figure 6:
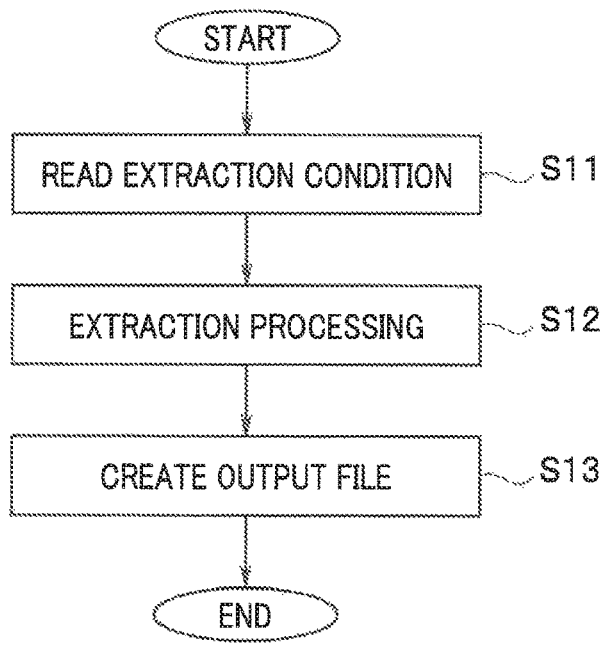
FIG. 6 is a flowchart showing an example of a processing flow of a relevant information extracting section according to the embodiment of the present invention.

FIG. 6 is a flowchart showing an example of a processing flow of the relevant information extracting section.

The relevant information extracting section 53 reads out an extraction condition based on the received error notification (S11).

FIG. 7 is a diagram showing an example of an extraction condition table configured to specify extraction conditions.

The extraction condition table TBL is included in the storage area 42b, and has eight items of a device name, an event, three extraction types, and three parameters. That is, the extraction condition table TBL configures an extraction condition storing section configured to store the extraction conditions for extracting relevant information.

Here, information of three extraction types corresponding to abnormal states specified by combinations of device names and events is stored as extraction conditions in the extraction condition table TBL. For the three extraction types, three types from a first extraction type having a highest priority to a third extraction type having a lowest priority are set in the extraction condition table TBL.

FIG. 7 shows that, with respect to the abnormal state of "Status Error" of the video switcher, the first extraction type is "B", a parameter value of the first extraction type is "5", the second extraction type is "C", a parameter value of the second extraction type is "1", the third extraction type is "A", and a parameter value of the third extraction type is "3".

Furthermore, as shown in FIG. 7, with respect to the abnormal states of "Status Error" of the pneumoperitoneum device and "Status Error" of the endoscope apparatus, the first extraction type to the third extraction type and parameter values of the first to third extraction types are set in the extraction condition table TBL. With respect to respective combinations of other devices and events, the three extraction types and the parameter values are likewise set as extraction conditions in the extraction condition table TBL.

As described above, the relevant information extracting section 53 extracts relevant information from log data according to an extraction condition specified from plural extraction conditions. A predetermined priority order is specified for the plural extraction conditions. As described later, the predetermined priority order specifies the order of transmission of the relevant information, or specifies the order of display of the relevant information in a portable terminal apparatus 63 which is a receiving apparatus configured to receive and display transmitted relevant information.

Here, the extraction type "A" specifies log data to be extracted in terms of time, and when the extraction condition is the extraction type "A" and the parameter value is "3", for example, log data over a predetermined time period just before an event occurs, for example, three minutes are extracted.

That is, the extraction type "A" as the extraction condition is a condition for setting as relevant information all log data over a predetermined time period before an occurrence time of error information.

The extraction type "B" specifies log data to be extracted in terms of the device name, and when the extraction condition is the extraction type "B" and the parameter value is "5", for example, log data over a predetermined number of times, for example, five operations for a device in which an event occurs are extracted. Note that the parameter may be time.

That is, the extraction type "B" which is the extraction condition is a condition for setting, as relevant information, log data over a predetermined number of times or a predetermined time period before occurrence of error information for a control target device related to the error information.

The extraction type "C" specifies log data to be extracted in terms of a predetermined group. When the extraction condition is the extraction type "C" and the parameter value is "1", for example, log data of a group 1 to which a device in which an event occurs belongs are extracted. One or more devices related to a device that has outputted an error notification is preset as one group. For example, in the case of the video switcher 34, the endoscope apparatus, the indoor camera 16, and the recorder 35 are set as one group as a device related to the video switcher 34.

That is, the extraction type "C" which is the extraction condition is a condition for setting, as relevant information, log data before occurrence of error information for a plurality of control target devices belonging to a group which is predetermined for a control target device related to the error information.

As described above, the extraction condition table TBL as the extraction condition storing section stores plural extraction conditions for each abnormal state. The relevant information extracting section 53 extracts relevant information from the log data according to a specified extraction condition from the plural extraction conditions.

Note that in this case, as shown in FIG. 7, the three extraction types corresponding to the combinations of the device names and the events are specified as the extraction conditions, but one item of a device name or the like may be used, or combinations other than the combination of the device name and the event may be used.

Furthermore, in this case, the three extraction conditions are specified according to each abnormal state as shown in FIG. 7, but one extraction condition may be specified.

Alternatively, the extraction condition may be at least one or at least two of the condition for setting, as the relevant information, all log data over a predetermined time period before occurrence of error information, the condition for setting, as the relevant information, log data over a predetermined number of times or a predetermined time period before occurrence of error information and the condition for setting, as the relevant information, log data before occurrence of error information for a plurality of control target devices belonging to a group predetermined for a control target device related to error information.

Furthermore, in this case, the three extraction types and the parameter values are set in the extraction condition table TBL for the respective combinations of the devices and the events, but may not be set for all the three extraction types, and four or more extraction types and parameter values may be set in the extraction condition table TBL.

Next, the relevant information extracting section 53 performs extraction processing for extracting log data according to an extraction condition read out in S11 (S12).

When no video signal of the foregoing video switcher 34 to the monitor 15 exits, the video switcher 34 is "Status Error". Therefore, in S11, information of the first extraction type to the third extraction type which correspond to "Status Error" of the video switcher 34, and parameter values of the first to third extraction types are read out from the extraction condition table TBL, and in S12, log data of the read-out three extraction types are extracted.

Since the first extraction type is "B" and the parameter value is "5", in the case of FIG. 4, log data over just-before five operations for the video switcher 34 are extracted.

FIG. 8 is a diagram showing log data to be extracted when the extraction type is "B". In FIG. 8, log data DD over just-before five operations for "video switcher" in the item "device name" serving as an extraction key DT are extracted.

Furthermore, since the second extraction type is "C" and the parameter value is "1", log data of operation on devices belonging to the group "1" of the device related to the video switcher 34 are extracted.

FIG. 9 is a diagram showing log data to be extracted when the extraction type is "C". In FIG. 9, log data DD of operation on devices belonging to the group "1" in the item "group" serving as the extraction key DT are extracted.

Furthermore, since the third extraction type is "A" and the parameter value is "3", in the case of FIG. 4, log data over three minutes just before an error notification are extracted.

FIG. 10 is a diagram showing log data to be extracted when the extraction type is "A". In FIG. 10, log data DD in the range of three minutes just before the error notification in the item "time" serving as the extraction key DT are extracted.

After the processing at S12, the relevant information extracting section 53 creates an output file (S13). In S13, the relevant information extracting section 53 creates plural output files including the extracted log data from the log data extracted in S12. In this case, since the three extraction conditions are set according to the contents of the error, three output files are created.

The example of FIG. 4 is an example in which the system controller 26 receives an error notification from the video switcher 34. Next, a case where the system controller 26 receives an error notification from the video processor 23 configuring the endoscope apparatus will be described.

FIG. 11 is a diagram showing another example of log data to be recorded in the hard disk drive of the system controller.

In FIG. 11, the video switcher 34 is assigned to a group 1, video devices other than the endoscope apparatus are assigned to a group 2, and the endoscope apparatus including the endoscope 33, the light source apparatus 24, the video processor 23 is assigned to a group 3, and energy apparatuses including the electric scalpel 31 and the electric scalpel apparatus 21 are assigned to a group 4.

FIG. 11 shows log data over a certain period. Details of a history of the log data in FIG. 11 are as follows.

A user operates the system controller 26 to perform setting of the video switcher 34, perform setting of outputting video of the indoor camera to the monitor 15, and perform operation of setting the color mode of an endoscopic image of 4K to a normal observation mode "1" in the video processor 23. Change of the color mode of the endoscopic image is notified from the video processor 23 to the light source apparatus 24.

Subsequently, log data indicating that a white balance button of the endoscope apparatus is operated and white balance has been completed is recorded.

Thereafter, the user operates the system controller 26 to set start of pneumoperitoneum on the pneumoperitoneum device 22, and then sets start of recording (REC) into the recorder 35.

Then, the user operates the system controller 26 to set the pneumoperitoneum pressure of the pneumoperitoneum device 22 to "5", and it is notified from the pneumoperitoneum device 22 to the system controller 26 that in response to the setting, the pneumoperitoneum pressure has been changed to "5".

Thereafter, the user operates the system controller 26 to set the color mode of the endoscope apparatus to an infrared light observation mode (2). As a result, the change in the color mode of the endoscopic image is notified from the video processor 23 to the light source apparatus 24, and the color mode is changed by arranging a filter for the infrared light observation mode.

Then, the user operates the system controller 26 to set the output value of the electric scalpel apparatus 21 to "5", and it is notified from the electric scalpel apparatus 21 to the system controller 26 that in response to the setting, the output value has been changed to "5".

Furthermore, it is notified that the user operates the operation portion of the front panel of the light source apparatus 24 and the color mode has been changed to the normal light observation mode "1".

The video processor 23 monitors the state of the light source apparatus 24, detects that the color mode of the light source apparatus 24 and the color mode of the video processor 23 do not coincide with each other, and thus outputs an error notification to the system controller 26.

As described above, when a nurse erroneously operates the operation panel of the light source apparatus 24 to change the color mode of the light source apparatus 24 to a color mode (color mode 1) corresponding to an ordinary light observation mode after the observation mode is changed from the normal light observation mode to a special light observation mode, an error notification is output from the video processor 23.

In FIG. 11, "color mode mismatch" is output as "Status Error" from the video processor 23 of the endoscope apparatus.

In the case of "color mode mismatch" of "Status Error" of the endoscope apparatus, the information of the first extraction type to the third extraction type set in the extraction condition table TBL and the respective parameter values are read out because of "Status Error" of the endoscope apparatus. In S12, log data of the three read-out extraction types are extracted.

Since the first extraction type is "B" and the parameter value is "3", in the case of FIG. 11, log data over last three operations for the endoscope apparatus are extracted.

FIG. 12 is a diagram showing log data extracted when the extraction type is "B". In FIG. 12, log data DD over just-before three operations for the "endoscope apparatus" in the item "device name" serving as the extraction key DT are extracted.

Furthermore, since the second extraction type is "C" and the parameter value is "3", in the case of FIG. 11, log data of operation on devices belonging to the group 3 of the device related to the endoscope apparatus are extracted.

FIG. 13 is a diagram showing log data extracted When the extraction type is "C". In FIG. 13, log data DD of operation on devices belonging to the group "3" in the item "group" serving as the extraction key DT are extracted.

Furthermore, since the third extraction type is "A" and the parameter value is "10", all log data DD over 10 minutes which are a predetermined time period just before an error notification are extracted.

FIG. 14 is a diagram showing log data extracted when the extraction type is "A". In FIG. 14, log data DD over 10 minutes just before the error notification in the item "time" serving as the extraction key DT are extracted.

Returning to FIG. 5, the system controller 26 performs mail transmission processing of transmitting an e-mail containing relevant information to a predetermined notification destination (S3). The processing of S3 configures a transmitting section configured to transmit extracted relevant information to a predetermined transmission destination. In other words, the processing of S3 configures a notifying section configured to notify the relevant information.

The text of an e-mail is a fixed sentence using a template, and the mail transmission processing is performed while three output files created in S13 are attached as attached files of the mail. A person in charge of maintenance who is a user can open and see the attached file of the received e-mail by operating the portable terminal apparatus 63.

Note that the log data may be output as sounds in the portable terminal apparatus 63.

Figure 15:
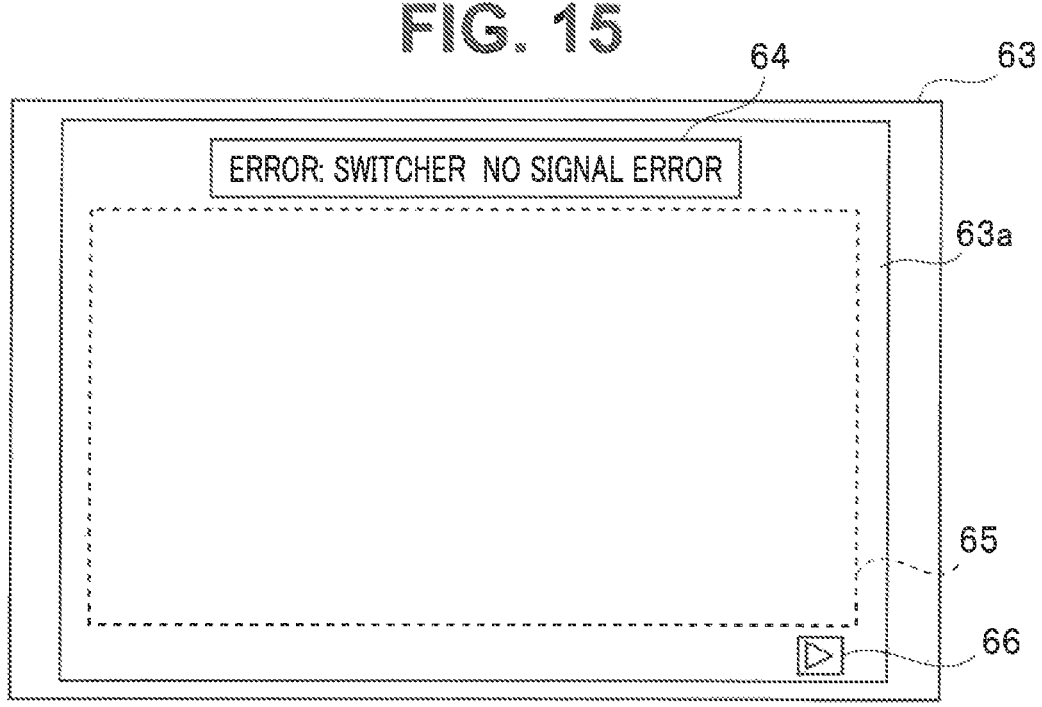
FIG. 15 is a diagram showing a display example of log data to be displayed on a display screen of a portable terminal apparatus according to the embodiment of the present invention.

FIG. 15 is a diagram showing a display example of log data displayed on a display screen of the portable terminal apparatus. The portable terminal apparatus 63 is a smartphone, a tablet, or the like, and the displaying section for displaying the display screen 63a has a touch panel.

Upon receiving an e-mail, the user can operate the portable terminal apparatus 63 to display the log data of the attached file on the display screen 63a.

An error content displaying section 64, a log data displaying section 65, and a page turning button 66 are displayed on the display screen 63a.

A message of "switcher no signal error" is displayed on the error content displaying section 64 to indicate an error content.

Log data of an output file are displayed on the log data displaying section 65, and not all log data, but only log data relating to an occurring error are displayed. Furthermore, when the user opens attached files, the three attached files are arranged according to a priority order, and log data extracted under an extraction condition having a highest priority can be first displayed. Here, the first extraction type has the highest priority, the second extraction type has a next highest priority to the first extraction type, and the third extraction type has a lowest priority.

The order of priority is determined according to an error content so that display is performed from log data for which a cause of occurrence of an error is easily found, and thus the user can easily find the cause of occurrence of the error promptly.

When it is impossible to find the cause of occurrence of the error even by watching the displayed log data, by touching the page turning button 66, the user can display log data extracted in the next priority order of the extraction condition of the log data being currently displayed on the log data displaying section 65.

Therefore, in the foregoing example, the log data extracted under the first extraction type (B) are first displayed, and by operating the page turning button 66, the log data extracted under the second extraction type (C) are displayed. The log data extracted under the third extraction type (A) are displayed by operating the page turning button 66 when the log data extracted under the second extraction type (C) are displayed.

Note that in this case, the three output files are transmitted while attached to one e-mail in the mail transmission processing of S3. However, an e-mail attached with only the output file of the log data extracted under the extraction type having the highest priority may be first sent, and then an e-mail attached with only the output file of the log data extracted under the extraction type having the next highest priority may be sent according to the operation of the foregoing page turning button 66. That is, the log data of the extraction condition of the next priority order may be transmitted according to a user's request.

As described above, the priority order for specifying the order of transmission of relevant information or the order of display of relevant information in a receiving apparatus configured to receive and display relevant information are specified in the three extraction conditions.

Accordingly, when an error notification from a device is received, log data relating to the error notification is extracted as relevant information and transmitted by e-mail to a person in charge of maintenance. When an error exists, the person in charge of maintenance can watch only log data which is an operation history related to the error together with the notification, so that the person in charge of maintenance can promptly grasp a cause such as an operation error or the like.

Transmission of Log Data When No Error Occurs

Furthermore, the operation of a device may fall into a state unintended by an operator or a nurse due to erroneous setting or operation although no error occurs during surgery.

In such a case, the user can transmit log data of a desired device to the person in charge of maintenance by performing a predetermined operation on the operation panel 28.

Figure 16:
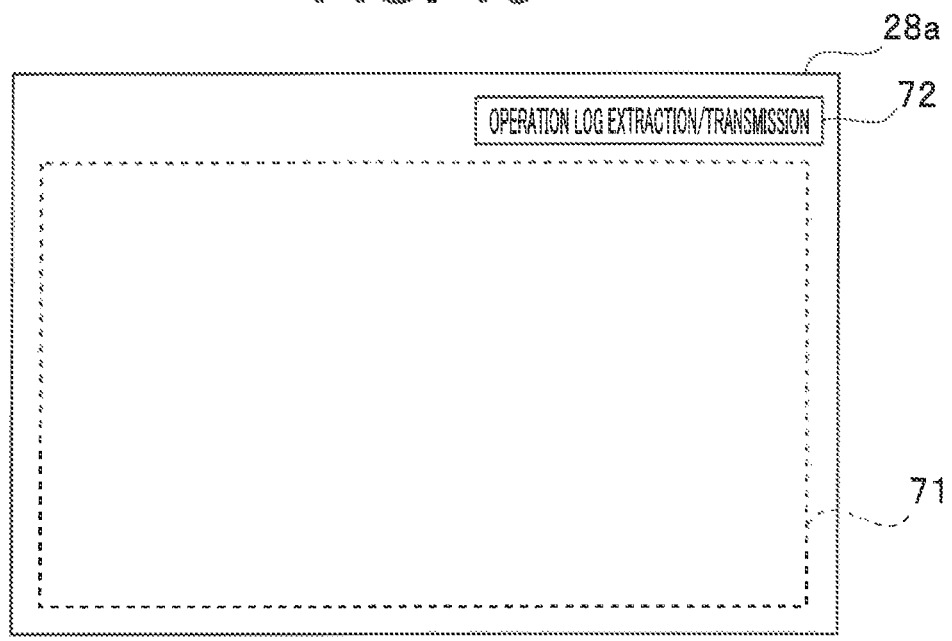
FIG. 16 is a diagram showing a display example of a displaying section of an operation panel 28 according to the embodiment of the present invention.

FIG. 16 is a diagram showing a display example on the displaying section of the operation panel 28.

The operation panel 28 is a displaying apparatus with a touch panel, and various kinds of information are displayed on the displaying section 28a of the operation panel 28, and operation buttons, etc. are also displayed. In FIG. 16, various kinds of information are displayed in an area 71 indicated by a dotted line, and various kinds of operation buttons are also displayed. An operation log extraction/transmission button 72 is displayed as an operation button on a part of the displaying section 28a.

When a user such as a nurse touches the operation log extraction/transmission button 72, a pull-down menu 73 is displayed.

Figure 17:
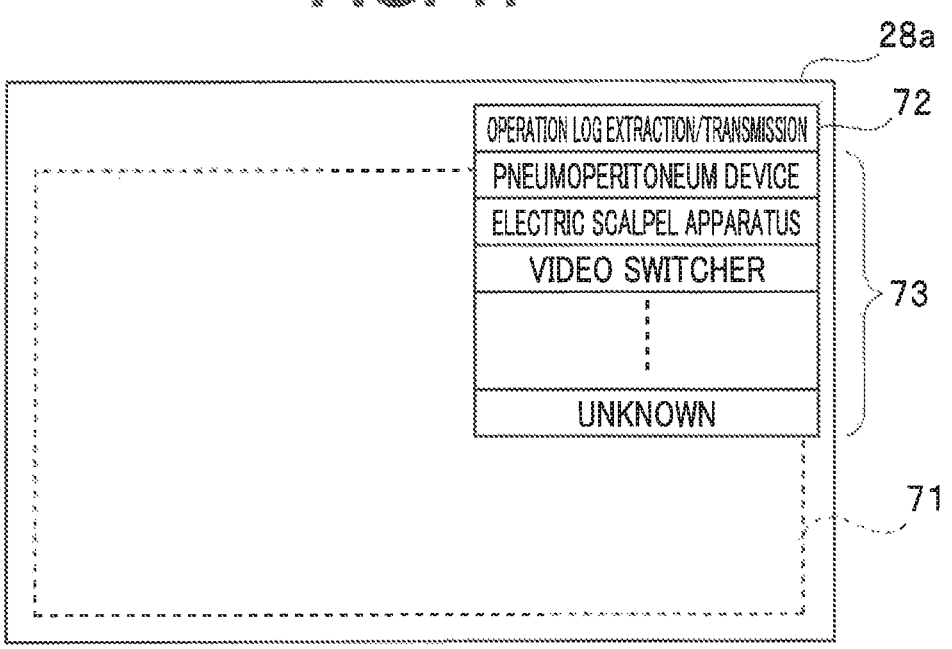
FIG. 17 is a diagram showing a display example of the displaying section on which a pull-down menu is displayed according to the embodiment of the present invention.

FIG. 17 is a diagram showing a display example of a displaying section on which the pull-down menu is displayed.

The pull-down menu 73 includes plural operation buttons of device names such as the pneumoperitoneum device and the electric scalpel apparatus.

For example, when the user wishes to transmit log data of operation on the pneumoperitoneum device, by touching the operation button of "pneumoperitoneum device", the log data of the operation on the pneumoperitoneum device are extracted from log data, and transmitted to an e-mail address of a person in charge of maintenance who has been registered in advance.

Figures 18, 19:
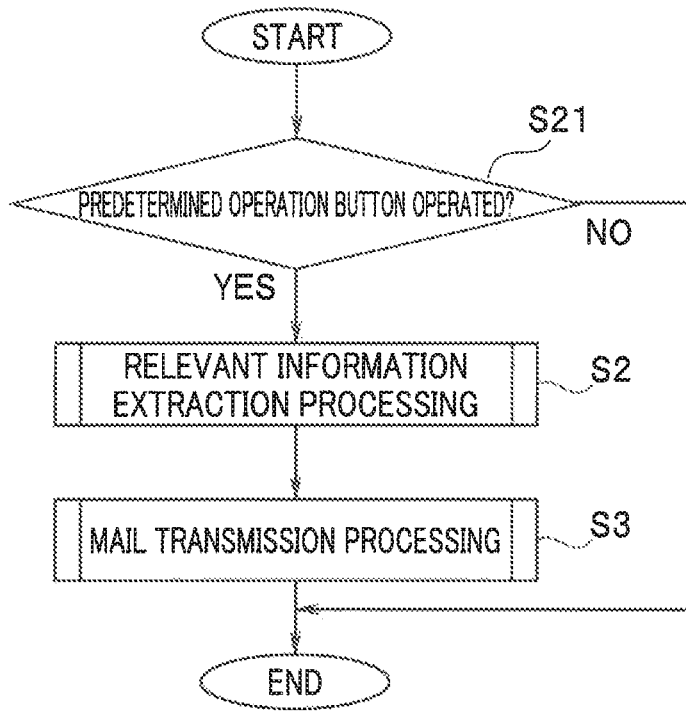
FIG. 18 is a flowchart showing an example of a processing flow of a system controller 26 according to the embodiment of the present invention.
FIG. 19 is a diagram showing an example of an extraction condition table that specifies extraction conditions according to the embodiment of the present invention.

FIG. 18 is a flowchart showing an example of the processing flow of the system controller 26.

The system controller 26 determines whether a predetermined operation button is operated (S21). Here, when the operation log extraction/transmission button 72 is toughed with a user's finger and a target device in the pull-down menu 73 is selected, it is determined that a predetermined operation button has been operated.

For example, when a user such as a nurse thinks that the output of the pneumoperitoneum device 22 is not equal to a desired output although no error notification from the pneumoperitoneum device 22 is output, the user touches the operation log extraction/transmission button 72 and touches the operation button of "pneumoperitoneum device" in the pull-down menu 73, whereby it is determined that the predetermined operation button is operated.

When the predetermined operation button has been not operated (S21: NO), no processing is executed.

When the predetermined operation button is operated (S21: YES), the system controller 26 performs the log data extraction processing of extracting relevant information relating to the operation button from the log data by the relevant information extracting section 53 (S2).

The log data extraction processing (52) is the same as the processing shown in FIG. 6, but a reference table at the time of reading the extraction condition is a table different from the extraction condition table TBL.

FIG. 19 is a diagram showing an example of the extraction condition table for specifying extraction conditions.

An extraction condition table TBL1 has two items of an operation button name and an extraction type.

In this case, information on the extraction types corresponding to the operation button names is stored in the extraction condition table TBL1. FIG. 19 shows that the extraction types for the video switcher, the pneumoperitoneum device, and the endoscope apparatus are "B", and the extraction type for "unknown" is "A". That is, information of the extraction types corresponding to the operation button names is stored in the extraction condition table TBL1 of FIG. 19.

The processing of S3 is the above-described transmission processing.

Therefore, upon receiving an instruction of extracting log data on a specified control target device, the relevant information extracting section 53 extracts relevant information relating to the specified control target device from the log data. Then, the relevant inhumation is transmitted to a predetermined address.

As described above, according to the foregoing embodiment, when abnormality occurs in a device used for surgery, it is possible to provide a central control apparatus configured to select and transmit log data relevant to the abnormality.

Furthermore, even when no abnormality occurs, the central control apparatus can transmit log data of operation on a device desired by the user, so that the user can promptly know finding or indication of a mistake of setting or the like.

Next, a modification will be described.

In the embodiment described above, log data extracted by the relevant information extracting section 53 are transmitted from the system controller 26 to the portable terminal apparatus 63 via the server 61 by e-mail, but the log data may be stored in the server 61 while a notification notifying only that the log data have been extracted is transmitted to the portable terminal apparatus 63 of the person in charge of maintenance by e-mail. The person in charge of maintenance who has received the notification can refer to the log data stored in the server 61.

Furthermore, the log data extracted by the relevant information extracting section 53 may be displayed on the displaying section of the operation panel 28 of the system controller 26. In this case, the displaying section of the operation panel 28 configures a notifying section configured to notify the extracted log data. The person in charge of maintenance can refer to the log data displayed on the displaying section of the operation panel 28.

Each "section" in the present specification is a conceptual one corresponding to each function of the embodiment, and does not necessarily correspond to specific hardware or software routine on a one-to-one basis. Accordingly, in the present specification, the embodiment has been described on the assumption of virtual circuit blocks (sections) having respective functions of the embodiment. In addition, as long as respective steps of each procedure in the present embodiment are not contrary to properties of the steps, the execution order of the steps may be changed, and plural steps may be executed at the same time, or the steps may be executed in a different order for each execution. Furthermore, all or some of the steps of each procedure in the present embodiment may be achieved by hardware.

The present invention is not limited to the foregoing embodiment, and various modifications, alterations and the like can be made without changing the subject matter of the present invention.

What is claimed is:

1. A central control apparatus comprising:
   a communicating device capable of communicating with a plurality of control target devices used in surgery;
   an extraction condition memory capable of storing extraction conditions related to abnormal states corresponding to types of the plurality of control target devices; and
   a processor including hardware,
   wherein the processor detects the abnormal states of the control target devices based on a communication result of the communicating device, performs recording processing for recording operation information relating to operation on the control target devices as log data into a predetermined storage apparatus, and upon detection of an abnormal state of any of the plurality of control target devices, extracts predetermined log data out of the recorded log data as relevant information according to an extraction condition stored in the extraction condition memory and corresponding to a type of a control target device for which the abnormal state is detected,
   the extraction conditions stored in the extraction condition memory include a plurality of extraction types that are different in priority order according to the types of the plurality of control target devices, and a plurality of parameter values, and
   the plurality of extraction types include a type for setting, as the relevant information, log data relating to the control target device for which the abnormal state is detected, and a type for setting, as the relevant information, log data relating to a plurality of control target devices belonging to a group containing the control target device for which the abnormal state is detected.

2. The central control apparatus according to claim 1, wherein the log data includes the operation information relating to the operation on the control target device and each identification information relating to the control target device.

3. The central control apparatus according to claim 1, wherein the priority order specifies a display order of the relevant information on a display apparatus configured to display the relevant information.

4. The central control apparatus according to claim 1, further comprising a notifying section configured to notify the extracted relevant information, wherein
   the notifying section is a transmitting section configured to transmit the extracted relevant information to a predetermined transmission destination, and
   the priority order specifies a transmission order of the relevant information in the transmitting section, or a display order of the relevant information in a receiving apparatus configured to receive and display the relevant information transmitted from the transmitting section.

5. The central control apparatus according to claim 1, wherein the plurality of extraction types further include a type for setting, as the relevant information, all log data over a predetermined time period before an occurrence time of the abnormal state.

6. The central control apparatus according to claim 1, wherein the plurality of parameters include a parameter for setting, as the relevant information, log data over a predetermined number of times or a predetermined time period before occurrence of the abnormal state, the log data relating to the control target device for which the abnormal state is detected.

* * * * *